(12) United States Patent
Yang (10) Patent No.: US 10,702,425 B2
(45) Date of Patent: Jul. 7, 2020

(54) FOLDED SIDE-LEAKAGE-PROOF ARC-SHAPED ELASTIC SANITARY PRODUCT WAINSCOT AND PRODUCTION LINE THEREFOR

(71) Applicant: Mingda Yang, Zhejiang (CN)

(72) Inventor: Mingda Yang, Zhejiang (CN)

( * ) Notice: Subject to any disclaimer, the term of this patent is extended or adjusted under 35 U.S.C. 154(b) by 475 days.

(21) Appl. No.: 15/490,227

(22) Filed: Apr. 18, 2017

(65) Prior Publication Data

US 2018/0078430 A1 Mar. 22, 2018

(30) Foreign Application Priority Data

Sep. 20, 2016 (CN) .......................... 2016 1 0833852
Sep. 20, 2016 (CN) .......................... 2016 1 0833855

(51) Int. Cl.
*A61F 13/00* (2006.01)
*B29C 39/00* (2006.01)
(Continued)

(52) U.S. Cl.
CPC .. *A61F 13/49406* (2013.01); *A61F 13/15739* (2013.01); *A61F 13/15747* (2013.01);
(Continued)

(58) Field of Classification Search
CPC .......... A61F 13/00; A61F 13/10; A61F 13/15; A61F 13/157; A61F 13/1573;
(Continued)

(56) References Cited

U.S. PATENT DOCUMENTS 5,611,790 A * 3/1997 Osborn, III ........... A61F 13/472
604/373
6,649,548 B1 * 11/2003 Shawver ................ A41D 31/02
442/398
2016/0166443 A1 * 6/2016 Arora ................ A61F 13/51113
604/378

FOREIGN PATENT DOCUMENTS

CN 204521234 U 8/2015

* cited by examiner

*Primary Examiner* — Jacob T Minskey
*Assistant Examiner* — Matthew Hoover
(74) *Attorney, Agent, or Firm* — Ladas & Parry LLP (57) ABSTRACT

The present invention relates to a folded side-leakage-proof arc-shaped elastic sanitary product wainscot and a production line therefor. After two sides of an elastic membrane under a tensile state are compounded with nonwoven fabric strips by hot pressing respectively, the elastic membrane rebounds and resets to impel the nonwoven fabric strips located on two sides of the elastic membrane to form a folded side-leakage-proof side wall. The elastic membrane is in the shape of a concave arc. The present invention has the following advantages: 1, the nonwoven fabric strips may be compounded with two sides of the elastic air-permeable membrane without a hot melt adhesive so as to ensure that the air permeability of the elastic air-permeable membrane and the nonwoven fabric strips is not affected by the hot melt adhesive; and 2, after two sides of the elastic air-permeable membrane under a tensile state are compounded with the nonwoven fabric strips, the elastic air-permeable membrane rebounds to impel the nonwoven fabric strips to form a required elastic folded side-leakage-proof side wall with the rebound and reset of the elastic air-permeable membrane. This side wall not only has a function of preventing liquid from flowing, but also greatly reduces a contact area between a sanitary napkin or a panty-shape diaper and a (Continued)

human body, such that the comfort level of the human body is greatly improved.

3 Claims, 3 Drawing Sheets (51) Int. Cl.
   B29D 99/00 (2010.01)
   B32B 3/00 (2006.01)
   B32B 5/00 (2006.01)
   B32B 27/00 (2006.01)
   A61F 13/494 (2006.01)
   B32B 3/08 (2006.01)
   B32B 3/26 (2006.01)
   B32B 3/28 (2006.01)
   B32B 5/02 (2006.01)
   B32B 27/12 (2006.01)
   B29C 39/14 (2006.01)
   A61F 13/15 (2006.01)
   A61F 13/49 (2006.01)
   B29L 31/00 (2006.01)
   B29L 31/48 (2006.01)

(52) U.S. Cl.
   CPC .. *A61F 13/15772* (2013.01); *A61F 13/49017* (2013.01); *B29C 39/148* (2013.01); *B29D 99/005* (2013.01); *B32B 3/08* (2013.01); *B32B 3/266* (2013.01); *B32B 3/28* (2013.01); *B32B 5/022* (2013.01); *B32B 27/12* (2013.01); *A61F 2013/15878* (2013.01); *A61F 2013/15918* (2013.01); *A61F 2013/15926* (2013.01); *A61F 2013/4948* (2013.01); *B29L 2031/4878* (2013.01); *B29L 2031/755* (2013.01); *B32B 2250/02* (2013.01); *B32B 2307/51* (2013.01); *B32B 2307/54* (2013.01); *B32B 2307/724* (2013.01); *B32B 2555/02* (2013.01)

(58) Field of Classification Search
   CPC ............ A61F 13/15739; A61F 13/1574; A61F 13/15747; A61F 13/1577; A61F 13/15772; A61F 13/40; A61F 13/49; A61F 13/49; A61F 13/4901; A61F 13/49017; A61F 13/494; A61F 13/494; A61F 13/49406; B29C 39/00; B29C 39/10; B29C 39/14; B29C 39/148; B29D 99/00; B29D 99/005; B32B 3/00; B32B 3/08; B32B 3/20; B32B 3/26; B32B 3/266; B32B 3/28; B32B 5/00; B32B 5/02; B32B 5/022; B32B 27/00; B32B 27/10; B32B 27/12
   See application file for complete search history.

FOLDED SIDE-LEAKAGE-PROOF ARC-SHAPED ELASTIC SANITARY PRODUCT WAINSCOT AND PRODUCTION LINE THEREFOR

TECHNICAL FIELD

The present invention relates to a folded side-leakage-proof arc-shaped sanitary product wainscot on which two non-woven fabric strips are compounded without using a hot melt adhesive and without stretching a non-woven fabric when the elastic air-permeable membrane is under a tensile state and which is formed after the elastic air-permeable membrane rebounds and resets and has a side-leakage-proof side wall, and a production line for the sanitary production wainscot. The folded side-leakage-proof arc-shaped sanitary product wainscot is mainly used for sanitary napkins and the crotch of panty-shape diapers and belongs to the field of sanitary product manufacturing.

BACKGROUND ART

A "leakage-proof sanitary napkin" (CN204521234 U) comprises a sanitary napkin body (100). An upper surface of the sanitary napkin body is provided with a drain layer. The middle part of the drain layer protrudes upward along a length direction and is constructed into an arc wainscot. The periphery of the arc wainscot is provided with at least one liquid guide groove which is constructed by a plurality of through holes formed in the drain layer and distributed along the circumferential direction of the arc wainscot. The periphery of the drain layer is provided with a flank. The junction between the flank and the drain layer is constructed into a liquid fender strip raised upward. An alarm device is arranged outside the liquid fender strip, the alarm device comprising an inductive switch, a power supply, a drive circuit and a buzzer. The inductive switch is used for connecting the drive circuit to the power supply in case that liquid is detected so as to drive the buzzer to produce sound. The leakage-proof sanitary product wainscot has the defects that: 1. the arc wainscot is a convex arc wainscot for a purpose of guiding liquid to two sides via the liquid guide groove, thereby neither solving the problem how to effectively reduce a contact surface between the female pudendum and the sanitary napkin, nor solving the problems on storage and suction of menstrual flow; and 2. the side-leakage-proof problem is not solved.

SUMMARY OF THE INVENTION

The purpose of design: a folded side-leakage-proof arc-shaped sanitary product wainscot on which two non-woven fabric strips are compounded without using a hot melt adhesive and without stretching a non-woven fabric when an elastic air-permeable membrane is under a tensile state and which is formed after the elastic air-permeable membrane rebounds and resets and has a side-leakage-proof side wall, and a production line for the sanitary product wainscot are designed to avoid the defects in the background art. The folded side-leakage-proof arc-shaped sanitary product wainscot is mainly used for sanitary napkins and the crotch of panty-shape diapers.

The scheme of design is adopted to achieve said purpose of design. In the structure design of the present invention: 1. the design in which a membrane surface of an elastic membrane is provided with numerous air-permeable holes is the first technical feature of the present invention. Such design lies in that: a phenomenon that a hot melt adhesive blocks air-permeable holes in the membrane surface of the elastic membrane because the elastic membrane is compounded with a non-woven fabric without a hot melt adhesive) under a tensile state, that is, the membrane surface of the elastic air-permeable membrane under a tensile state is directly compounded by hot melting with the non-woven fabric, is avoided. Secondly, the elastic air-permeable membrane has the advantages: an air-impermeable elastic membrane can be changed into an air-permeable membrane, and the elastic membrane full of air-permeable holes has large tensile rate and good elasticity, such that the tensile rate of the elastic air-permeable membrane can be effectively improved. More importantly, first, the elastic air-permeable membrane of the present invention can be adopted to overcome the defects of complicated manufacturing equipment, high cost, complicated manufacturing process and low efficiency resulting from rubber strings for preventing side leakage, as well as elasticity decrease, poor air permeability and poor comfort level of a sanitary napkin resulting from the adoption of an adhesive for locating the rubber strings, in the existing wainscots for sanitary napkins and panty-shape diapers. 2. The design in which the elastic membrane provided with numerous air-permeable holes is compounded with a non-woven fabric by hot pressing under a tensile state is the second technical feature of the present invention. Such design lies in that: the non-woven fabric has favorable water tightness, but has little elasticity which may be negligible basically. According to the present invention, two sides of the elastic membrane under a tensile state are respectively compounded with non-woven fabric strips by hot pressing and then rebounds to form a folded side-leakage-proof side wall. When a sanitary napkin or panty-shape diaper formed by the side-leakage-proof side wall is used, a nest-shaped structure can be formed. This nest-shaped structure not only effectively reduces the contact area between the surface of the sanitary napkin and the pudendum of the human body (the periphery of the nest-shaped wainscot contacts the pudendum of the human body only), but also solves the problems on collection and suction of excrement. 3. The design in which edges of negative-pressure suction orifices formed by the air-permeable holes in the elastic membrane are of a boss opening structure is the third technical feature of the present invention. Such design lies in that: in a negative-pressure suction punching process, edges of negative-pressure suction orifices (at one negative-pressure air outlet end) in the elastic membrane surface are shaped as boss openings; the boss openings are just like a plurality of hole-shaped supports distributed on the elastic membrane surface; because opening portions of the hole-shaped supports are higher than the membrane surface, a suction core layer is combined with the boss openings of the elastic membrane surface in a form of a plurality of opening-shape points when the opening portions of the hole-shaped supports contact the suction core layer of the sanitary napkin, such that multiple paths of hollow multi-point supports which are communicated to one another are formed between the suction core layer and the elastic membrane; and therefore, not only the air permeability is very good, but also the precedent of hollow multi-point supports is created. 4. The design in which multiple pairs of elastic air-permeable membrane stretching roll sets are transversely distributed at one side of the elastic air-permeable cast membrane forming roll sets in sequence, and compound forming roll sets are transversely located at one side of the elastic air-permeable membrane stretching roll set at the tail end among multiple pairs of elastic air-permeable membrane stretching roll sets is the fourth technical feature of the present invention. Such design lies in that: transverse arrangement of the elastic air-permeable membrane stretching roll sets and the elastic air-permeable cast membrane forming roll sets not only can avoid the phenomenon that the thickness of the elastic air-permeable membrane is uneven caused by the suction force to the elastic membrane from gravity in case of vertical arrangement therebetween, but also can realize hot-pressing compounding between a single surface or double surfaces of the elastic air-permeable membrane and a non-woven fabric while the elastic air-permeable membrane is stretched. 5. The design in which the surface of a polished roll in the elastic air-permeable cast membrane forming roll set is provided with a layer of high-temperature resistant anti-adhesion nano-coating is the fifth technical feature of the present invention. Such design lies in that: high-elasticity macromolecular resin particles for manufacturing the elastic membrane are likely to generate roll sticking and adhesion phenomena due to relatively large viscosity and relatively high temperature under a molten state, thereby being not good for forming of the elastic air-permeable membrane. According to the present invention, the polished roll in the elastic air-permeable cast membrane forming roll set is designed into a high-temperature resistance anti-adhesion nano-roll, such that not only the phenomenon of sticking or adhesion between the high-elasticity macromolecular resin particles and the polished roll under a molten state is avoided, but also the high-temperature resistant requirement is met, and therefore, the quality of the primarily formed elastic air-permeable membrane is ensured. 6. The design in which a roll surface of a negative-pressure punching roll in the elastic air-permeable cast membrane forming roll set is full of negative-pressure suction orifices is the sixth technical feature of the present invention. Such design lies in that: because the negative-pressure suction orifices filled in the roll surface of the negative-pressure punching roll are communicated with a negative-pressure cavity in the negative-pressure punching roll through respective channel (the negative-pressure cavity is connected with a negative-pressure source through a pipeline), a membrane surface of the elastic membrane passing through the negative-pressure punching roll is sucked into an elastic membrane surface full of air-permeable holes by means of the negative-pressure suction orifices under the action of negative-pressure airflow; and edges of back orifices of the air-permeable holes raise to be higher than the membrane surface, thereby forming a negative-pressure punched elastic air-permeable membrane. 7. The design in which the surface of a polished roll and the surface of a rubber roll in the elastic air-permeable membrane stretching roll set is provided with a layer of high-temperature resistant anti-adhesion nano-coating respectively is the seventh technical feature of the present invention. Such design lies in that: the polished roll is designed into a high-temperature resistant anti-adhesion nano-roll, such that not only the phenomenon of sticking or adhesion between the high-elasticity macromolecular resin particles and the polished roll under a molten state is avoided, but also the high-temperature resistant requirement is met, and therefore, the quality of the primarily formed elastic air-permeable membrane is ensured; and the roll surface of the rubber roll adopts an elastic high-temperature resistant anti-adhesion coating, such that the roll surface of the rubber roll is anti-sticking, but also has favorable adherence and ensures the relative consistency of the stretching coefficient of the elastic air-permeable membrane. 8. The design in which the elastic air-permeable membrane stretching roll set is internally provided with an electric heating tube and a temperature sensor is the eighth technical feature of the present invention. Such design lies in that: because the non-woven fabric and the elastic air-permeable membrane are compounded by hot pressing, rather than a hot melt adhesive in the present invention, it is crucial to ensure the membrane surface temperature of the elastic air-permeable membrane in a stretching process, and therefore the electric heating tube and the temperature sensor are arranged in the polished roll and the rubber roll in the present invention; and the temperature sensor transmits temperature data acquired in real time to a PLC controller and compares the same with hot-adhesion data of the membrane surface of the elastic air-permeable membrane in the PLC controller to further control a working temperature of the electric heating tubes in the polished roll and the rubber roll, such that the elastic air-permeable membrane is at a temperature state of hot-pressing adhesion before being compounded with the non-woven fabric, and therefore, reliable hot-pressing compounding between a single surface or double surfaces of the elastic air-permeable membrane and the non-woven fabric is ensured. 9. The design in which the surface of a concave-convex roll and the surface of a convex-concave roll in the elastic air-permeable membrane stretching roll set are provided with a layer of high-temperature resistant anti-adhesion nano-coating respectively is the ninth technical feature of the present invention. Such design lies in that: the concave-convex roll and the convex-concave roll in the compound forming roll set have a function of transmitting and stretching the elastic air-permeable membrane and a function of compounding the elastic air-permeable membrane and the non-woven fabric under a tensile state, and therefore, the compound forming roll set not only has the characteristics of anti-sticking and high adherence, but also has a function of heat-preservation hot-pressing compounding. Therefore, the roll surface of the compound forming roll set is provided with a layer of high-temperature resistant anti-adhesion elastic nano-coating. The high-temperature resistant anti-adhesion elastic nano-coating prevents the adhesion between the elastic air-permeable membrane and the roll surface on the premise of not changing the tensile state of the elastic air-permeable membrane, realizes elastic hot-pressing compounding between the non-woven fabric and the elastic air-permeable membrane and ensures constant handfeel comfort level of the surface of the compounded non-woven fabric, because of having the characteristics of high-temperature resistance, anti-sticking and good adherence. The electric heating tube and the temperature sensor arranged in each of the concave-convex roll and the convex-concave roll are used to acquire and control temperature data via the PLC controller. Because being internally provided with hot-pressing adhesion temperature parameters of the elastic air-permeable membrane, the PLC controller controls the temperature of the elastic air-permeable membrane stretching roll sets to change within a hot-pressing adhesion temperature range of the elastic air-permeable membrane by acquiring and comparing the temperatures of the elastic air-permeable membrane stretching roll sets, thereby keeping a compounding temperature of the compound forming roll sets within an optimal set range. 10. The design in which an elastic air-permeable cast membrane forming roll set and an elastic air-permeable cast membrane forming roll set are provided with a revolution speed sensor respectively is the tenth technical feature of the present invention. Such design lies in that: because the revolution speeds of the elastic air-permeable cast membrane forming roll set and the elastic air-permeable membrane stretching roll set are controlled by the PLC controller, the PLC controller can control a difference between the revolution speeds of the elastic air-permeable cast membrane forming roll set and the elastic air-permeable membrane stretching roll set in real time by acquiring data of the revolution speed sensors on the elastic air-permeable cast membrane forming roll set and the elastic air-permeable membrane stretching roll set and comparing the data with a detection control software package where the tensile rate of the elastic air-permeable membrane corresponds to the revolution speed of the elastic air-permeable membrane stretching roll set in the PLC controller, thereby ensuring that the required tensile rate of the elastic air-permeable membrane is controlled within a set range.

Technical Solution 1: a folded side-leakage-proof arc-shaped elastic sanitary product wainscot is provided, wherein after two sides of an elastic membrane under a tensile state are respectively compounded with nonwoven fabric strips by hot pressing, the elastic membrane rebounds and resets to impel the nonwoven fabric strips located on two sides of the elastic membrane to form a folded side-leakage-proof side wall. The elastic membrane is in the shape of a concave arc.

Technical Solution 2: a forming method for a folded side-leakage-proof arc-shaped elastic sanitary product wainscot is provided, wherein an elastic membrane or an elastic air-permeable membrane is prepared from elastic macromolecular resin particles under a molten state via a membrane forming process, or an elastic punched air-permeable membrane is formed from the elastic membrane by punching with a membrane punching roll set; and after two sides of the elastic punched air-permeable membrane or the elastic air-permeable membrane under a tensile state are respectively compounded with nonwoven fabrics by hot pressing, the elastic punched air-permeable membrane or the elastic air-permeable membrane rebounds and impels the nonwoven fabrics at two sides thereof to form a folded side-leakage-proof side wall with the rebound of the elastic punched air-permeable membrane or elastic air-permeable membrane, wherein the elastic membrane located between the nonwoven fabric strips is in the shape of a concave arc.

Technical Solution 3: a production line for a folded side-leakage-proof arc-shaped elastic sanitary product wainscot is provided, comprising a PLC controller, wherein elastic air-permeable cast membrane forming roll sets are arranged below an elastic macromolecular resin cast membrane head, multiple pairs of longitudinal elastic air-permeable membrane stretching roll sets are transversely distributed at one side of the elastic air-permeable cast membrane forming roll sets in sequence, compound forming roll sets are transversely positioned at one side of the elastic air-permeable membrane stretching roll set at the tail end among the multiple pairs of elastic air-permeable membrane stretching roll sets, and roll surfaces of the compound forming roll sets are full of circular grooves and convex points which are matched in a form of concave points and convex points.

Technical Solution 4: a manufacturing method for an elastic air-permeable arc-shaped folded side-leakage-proof non-woven fabric is provided, wherein elastic macromolecular resin particles are cast into an elastic membrane via an elastic macromolecular resin cast membrane head, the elastic membrane is exported via elastic air-permeable cast membrane forming roll sets to form an elastic punched air-permeable membrane whose membrane surface is distributed with numerous air-permeable holes, the elastic punched air-permeable membrane is longitudinally stretched in an S shape via multiple pairs of elastic air-permeable membrane stretching roll sets and then enters compound forming roll sets together with an unstretched underlayer non-woven fabric and an unstretched face layer non-woven fabric located on two sides of the elastic punched air-permeable membrane to be compounded by hot pressing and then exported, and then, the face layer non-woven fabric and the underlayer non-woven fabric located on two sides of the elastic punched air-permeable membrane form the elastic arc-shaped folded side-leakage-proof non-woven fabric with the rebound and reset of the elastic punched air-permeable membrane.

Technical Solution 5: a manufacturing method for an elastic air-permeable arc-shaped folded side-leakage-proof non-woven fabric is provided, wherein elastic macromolecular resin particles are cast into an elastic membrane via an elastic macromolecular resin cast membrane head, the elastic membrane is exported via elastic air-permeable cast membrane forming roll sets to form an elastic air-permeable membrane whose membrane surface is distributed with numerous air-permeable holes, the elastic punched air-permeable membrane is longitudinally stretched in an S shape via multiple pairs of elastic air-permeable membrane stretching roll sets and then enters compound forming roll sets together with unstretched non-woven fabric strips located on two sides of the elastic punched air-permeable non-woven fabric to be compounded by hot pressing and then exported, and then, the non-woven fabric strips located on two sides of the elastic punched air-permeable membrane form an elastic arc-shaped wainscot, having a side-leakage-proof side wall, for sanitary napkins or panty-shape diapers with the rebound and reset of the elastic punched air-permeable membrane.

Compared with the background art, the present invention has the following advantages: 1, the nonwoven fabric strips may be compounded with two sides of the elastic air-permeable membrane without a hot melt adhesive so as to ensure that the air permeability of the elastic air-permeable membrane and the nonwoven fabric strips is not affected by the hot melt adhesive; 2, after two sides of the elastic punched air-permeable membrane or the elastic air-permeable membrane under a tensile state are respectively compounded with the nonwoven fabric strips, the elastic punched air-permeable membrane or the elastic air-permeable membrane rebounds to impel the nonwoven fabric strips to form the required elastic folded side-leakage-proof side wall with the rebound and reset of the elastic punched air-permeable membrane or the elastic air-permeable membrane, and this side wall not only has a function of preventing liquid from flowing, but also greatly reduces a contact area between a sanitary napkin or a panty-shape diaper and a human body, such that the comfort level of the human body is greatly improved; 3, the design in which edges of negative-pressure suction orifices formed by the air-permeable holes in the elastic punched air-permeable membrane are of a boss opening structure realizes multi-opening point combination between the elastic air-permeable membrane and a suction core layer, and therefore, not only the air permeability is very good, and the precedent of hollow multi-point supports is created; 4, the design in which the polished roll in the elastic air-permeable cast membrane forming roll set is provided with a high-temperature resistant anti-adhesion nano-coating not only solves the phenomenon of sticking or adhesion between the high-elasticity macromolecular resin particles under a molten state and the polished roll, but also meets a high-temperature resistant requirement; 5, the design in which the surface of the polished roll and the surface of the rubber roll in the elastic air-permeable membrane stretching roll set are coated with a high-temperature resistant anti-adhesion coating respectively realizes anti-sticking and ensures the relative consistency of the stretching coefficient of the elastic air-permeable membrane; 6, the design in which the elastic air-permeable membrane stretching roll set is internally provided with an electric heating tube and a temperature sensor ensures the elastic air-permeable membrane is at a required temperature state when being compounded with the non-woven fabric by hot pressing, and realizes reliable compounding between a single surface or double surfaces of the elastic air-permeable membrane and the non-woven fabric and the manufacturing of the compounded elastic air-permeable arc-shaped folded composite non-woven fabric; 7, the design in which the compound roll surfaces of the compound forming roll sets are coated with a layer of high-temperature anti-adhesion elastic nano-coating respectively realizes elastic compression-joint compounding between the non-woven fabric and the elastic air-permeable membrane and ensures constant handfeel comfort level of the surface of the compound non-woven fabric; 8, the design in which the elastic air-permeable cast membrane forming roll set and the elastic air-permeable membrane stretching roll set are provided with a revolution speed sensor respectively ensures that the required tensile rate of the elastic air-permeable membrane is controlled within a set range; and 9, the design of a punched elastic air-permeable membrane not only ensures that the elastic membrane has a ventilation function and the characteristics of high elasticity and large tensile rate, but also greatly increases the tensile rate.

DETAILED DESCRIPTIONS OF THE PREFERRED EMBODIMENTS

Figure 1:
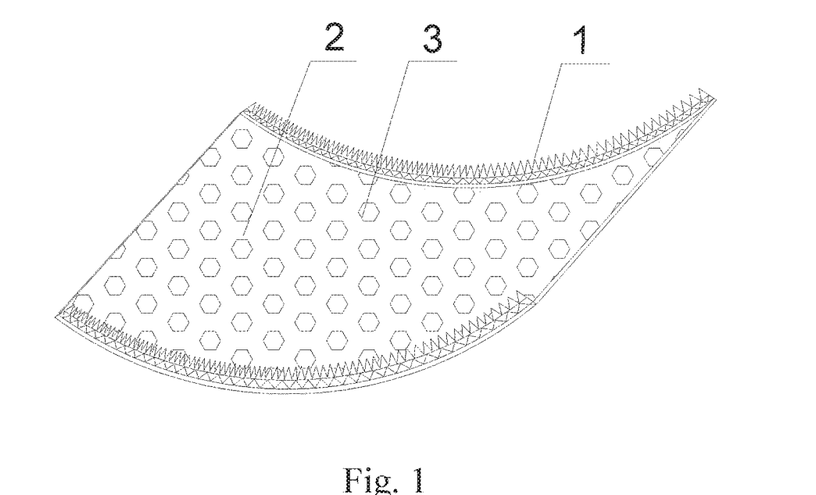
FIG. 1 is the first structural schematic drawing of the folded side-leakage-proof arc-shaped elastic sanitary product wainscot.
Figure 2:
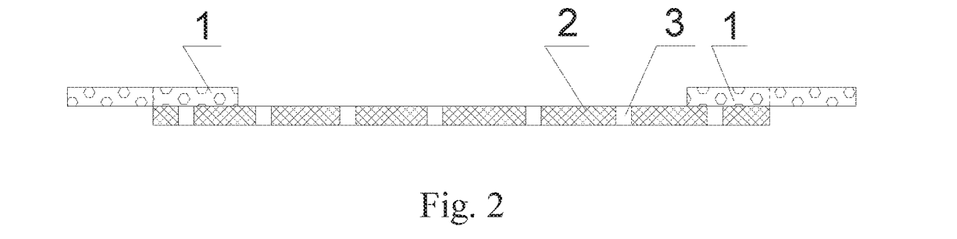
FIG. 2 is a cross-sectional structural schematic drawing before rebound and reset after stretching in FIG. 1.
Figure 3:
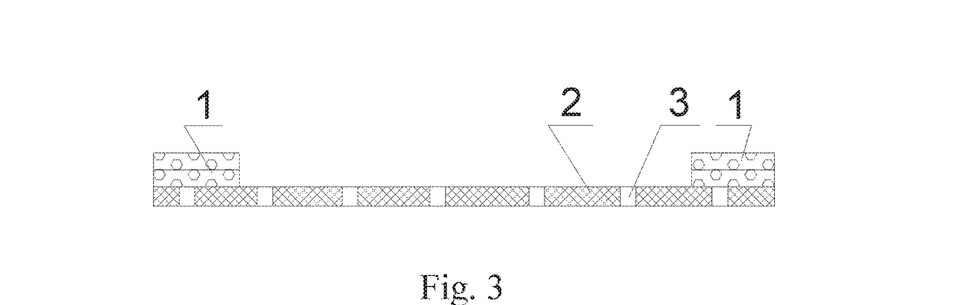
FIG. 3 is a structural schematic drawing before rebound and reset after stretching and after overlaying of the non-woven fabrics in FIG. 2.

Embodiment 1: refer to FIGS. 1-3. A folded side-leakage-proof arc-shaped elastic sanitary product wainscot, wherein after two sides of an elastic membrane 2 under a tensile state are respectively compounded with nonwoven fabric strips 1 by hot pressing, non-woven fabric strips compounded at two sides of the elastic membrane by hot pressing are folded in two layers, the elastic membrane rebounds and resets to impel the nonwoven fabric strips located on two sides of the elastic membrane to form a folded side-leakage-proof side wall, wherein the elastic membrane 2 located between the nonwoven fabric strips is in the shape of a concave arc. The tensile rate of the elastic air-permeable membrane ranges from 50% to 500% and comprises an end value.

Embodiment 2: based on Embodiment 1, the elastic membrane is an elastic punched air-permeable membrane, and air-permeable holes in the membrane surface of the elastic punched air-permeable membrane are conical holes 3.

Embodiment 3: based on Embodiment 1, the elastic membrane is an elastic air-permeable membrane. The elastic air-permeable membrane is formed from an elastic membrane composed of organic components and inorganic components under a tensile state.

Figure 4:
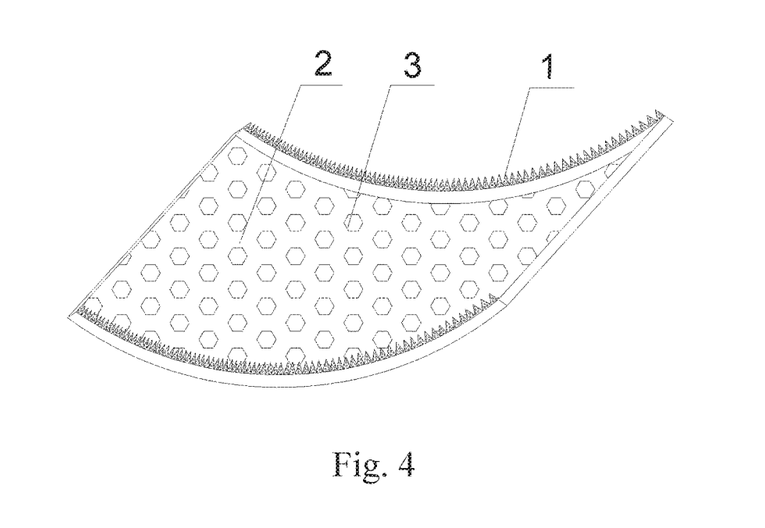
FIG. 4 is the second structural schematic drawing of the folded side-leakage-proof arc-shaped elastic sanitary product wainscot.
Figure 5:
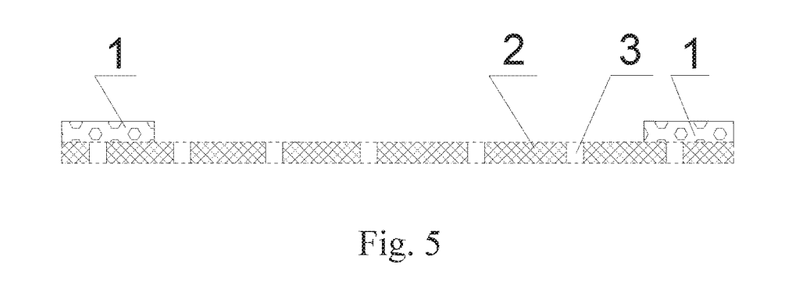
FIG. 5 is a cross-sectional structural schematic drawing before rebound and reset after stretching in FIG. 2.

Embodiment 4: refer to FIGS. 4-5. Based on Embodiment 1, two sides of the elastic membrane 2 under a tensile state are respectively compounded with non-woven fabric strips 1 by hot pressing, and each non-woven fabric strip 1 compounded by hot pressing is a single-layer strip.

Figure 6:
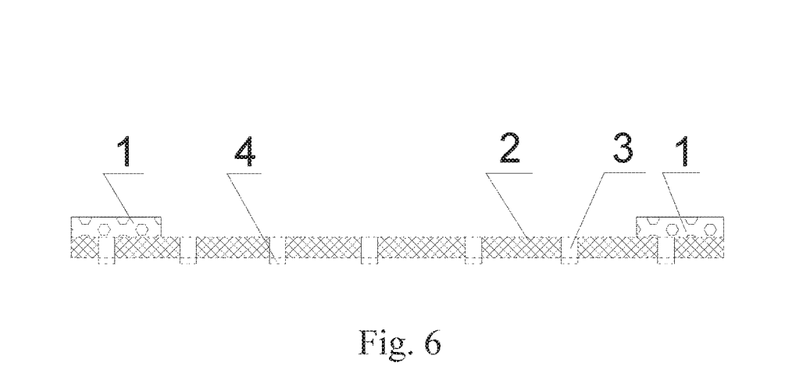
FIG. 6 is a cross-section structural schematic drawing in which the air-permeable holes of the elastic air-permeable membrane have boss eaves and do not rebound and reset after stretching.

Embodiment 5: refer to FIG. 6. Based on Embodiments 1, 2 and 4, air-permeable holes in the elastic air-permeable membrane (2) are punched by negative-pressure suction, and orifice edges (4) are higher than the membrane surface.

Embodiment 6: based on above embodiments, a forming method for a folded side-leakage-proof arc-shaped elastic sanitary product wainscot is provided, wherein an elastic membrane 2 or an elastic air-permeable membrane is prepared from elastic macromolecular resin particles under a molten state via a membrane forming process, or an elastic punched air-permeable membrane is formed from the elastic membrane by punching with a membrane punching roll set; and after two sides of the elastic punched air-permeable membrane or the elastic air-permeable membrane under a tensile state are respectively compounded with nonwoven fabrics 1 by hot pressing, the elastic punched air-permeable membrane or the elastic air-permeable membrane rebounds and impels the nonwoven fabrics 1 at two sides thereof to form a folded side-leakage-proof side wall with the rebound of the elastic punched air-permeable membrane or the elastic air-permeable membrane, wherein the elastic membrane 2 located between the nonwoven fabric strips is in the shape of a concave arc. The membrane forming process refers to a cast membrane forming and punching process. The cast membrane forming and punching process is composed of a cast membrane head and a membrane forming and punching device. The membrane forming and punching device is composed of negative-pressure suction orifice roll sets, or concave-convex knife roll sets.

Figure 7:
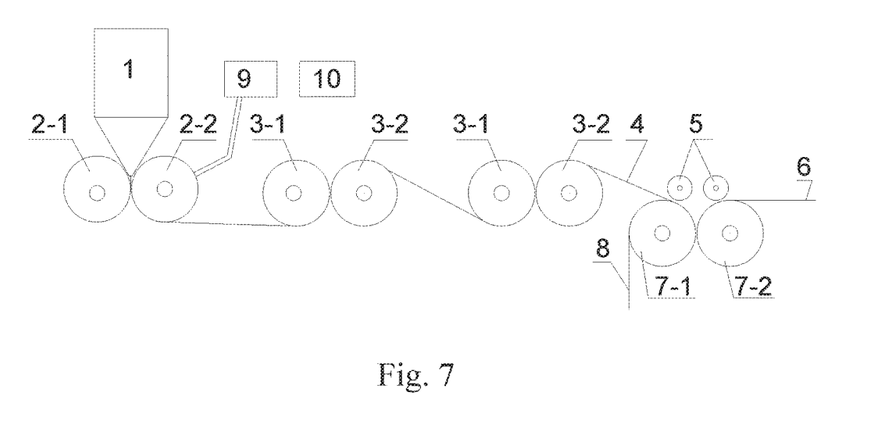
FIG. 7 is a structural schematic drawing of a production line for the folded side-leakage-proof arc-shaped elastic sanitary product wainscot.

Embodiment 7: refer to FIG. 7. A production line for a folded side-leakage-proof arc-shaped elastic sanitary product wainscot comprises a PLC controller 10, wherein elastic air-permeable cast membrane forming roll sets 2-1 and 2-2 are arranged below an elastic macromolecular resin cast membrane head 1, multiple pairs of longitudinal elastic air-permeable membrane stretching roll sets 3-1 and 3-2 are transversely distributed at one side of the elastic air-permeable cast membrane forming roll sets in sequence, compound forming roll sets 7-1 and 7-2 are transversely positioned at one side of the elastic air-permeable membrane stretching roll sets 3-1 and 3-2 at the tail end among the multiple pairs of elastic air-permeable membrane stretching roll sets, and roll surfaces of the compound forming roll sets 7-1 and 7-2 are full of circular grooves and convex points which are matched in a form of concave points and convex points. The elastic air-permeable membrane stretching roll set is composed of a polished roll 3-1 and a rubber roll 3-2, and a fit clearance between the polished roll 3-1 and a rubber roll 3-2 is less than the thickness of the stretched elastic air-permeable membrane.

The negative-pressure elastic air-permeable cast membrane forming roll sets 2-1 and 2-2 and the elastic air-permeable membrane stretching roll sets 3-1 and 3-2 are provided with a revolution speed sensor respectively, and a difference between the revolution speeds of the revolution speed sensors is controlled by the PLC controller. The PLC controller is internally provided with a detection control software package where the tensile rate of the elastic air-permeable membrane corresponds to the revolution speeds of the elastic air-permeable membrane stretching roll sets 3-1 and 3-2.

Embodiment 8: based on Embodiment 7, the elastic air-permeable cast membrane forming roll set is a negative-pressure punched and cast membrane forming roll set, or a concave-convex point punched and cast membrane forming roll set. The negative-pressure punched and cast membrane forming roll set is composed of a polished roll 2-1 and a negative-pressure punching roll 2-2; and the roll surface of the negative-pressure punching roll 2-2 is full of negative-pressure suction orifices which are communicated with a negative-pressure cavity in the negative-pressure punching roll via respective channel, and the negative-pressure cavity is communicated with a negative-pressure suction source 9 through a connecting pipe.

Embodiment 9: based on Embodiment 7, the concave-convex point punched and cast membrane forming roll set is composed of a conical groove roll and a conical convex cone roll which are matched with each other.

Embodiment 10: based on Embodiment 7, the roll surface of the polished roll 2-1 is provided with a layer of high-temperature resistant anti-adhesion nano-coating. The conical groove roll and the conical convex cone roll are provided with a layer of high-temperature resistant anti-adhesion nano-coating respectively. The elastic air-permeable membrane stretching roll set is composed of a polished roll 3-1 and a rubber roll 3-2, and the surface of the polished roll 3-1 and the surface of the rubber roll 3-2 are provided with a layer of high-temperature resistant anti-adhesion nano-coating respectively. The high-temperature resistant anti-adhesion nano-coating on the roll surface of the rubber roll 3-2 is an elastic layer. The compound forming roll set is composed of a conical groove roll 7-1 and a conical convex cone roll 7-2, and the surface of the conical groove roll 7-1 and the surface of the conical convex cone roll 7-2 are coated with a high-temperature resistant anti-adhesion nano-coating respectively.

Embodiment 11: based on Embodiment 7, the polished roll 3-1 and the rubber roll 3-2 in the elastic air-permeable membrane stretching roll set are provided with an electric heating tube and a temperature sensor respectively, wherein the temperature setting of the electric heating tubes is controlled by temperature data acquired by the temperature sensor and the PLC controller. The roll set at the tail end of multiple pairs of elastic air-permeable membrane stretching roll sets 3-1 and 3-2 is a temperature control roll set and a polished roll in the temperature control roll set is provided with an electric heating tube and a temperature sensor, wherein the temperature setting of the electric heating tube is controlled by temperature data acquired by the temperature sensor and the PLC controller. The conical groove roll 7-1 and the conical convex cone roll 7-2 are internally provided with an electric heating tube and a temperature sensor respectively, wherein the temperature setting of the electric heating tubes is controlled by temperature data acquired by the temperature sensor and the PLC controller. The PLC controller is internally provided with hot-pressing adhesion temperature parameters of the elastic air-permeable membrane, and controls the temperature of the elastic air-permeable membrane stretching roll sets to change within a hot-pressing adhesion range of the elastic air-permeable membrane by comparing the parameters with the temperature of the elastic air-permeable membrane stretching roll sets.

Embodiment 12: based on Embodiment 7, a manufacturing method for an elastic air-permeable arc-shaped folded side-leakage-proof non-woven fabric is provided, wherein elastic macromolecular resin particles are cast into an elastic membrane via an elastic macromolecular resin cast membrane head, the elastic membrane is exported via elastic air-permeable cast membrane forming roll sets 2-1 and 2-2 to form an elastic punched air-permeable membrane 4 whose membrane surface is distributed with numerous air-permeable holes, the elastic air-permeable membrane 4 is longitudinally stretched in an S shape via multiple pairs of elastic air-permeable membrane stretching roll sets and then enters compound forming roll sets 7-1 and 7-2 together with an unstretched underlayer non-woven fabric 8 and an unstretched face layer non-woven fabric 6 located on two sides of the elastic punched air-permeable membrane to be compounded by hot pressing and then exported, and then, the face layer non-woven fabric 6 and the underlayer non-woven fabric 8 located on two sides of the elastic punched air-permeable membrane 4 form the elastic arc-shaped folded side-leakage-proof non-woven fabric with the rebound and reset of the elastic punched air-permeable membrane. The tensile rate of the elastic air-permeable membrane ranges from 50% to 500%.

Figure 8:
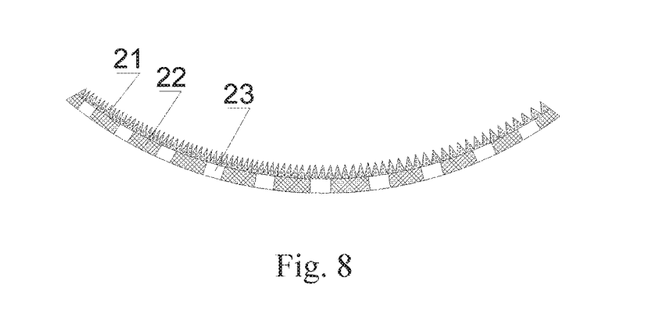
FIG. 8 is a structural schematic drawing of a folded air-permeable folded composite non-woven fabric manufactured by adopting the wainscot in FIG. 1.

Example 1: refer to FIG. 8. An electric arc-shaped air-permeable folded sanitary napkin wainscot, wherein after being thermally compounded with a non-woven fabric 21, the elastic membrane 22 under a tensile state resets and impels the non-woven fabric to form a folded concave-arc-shaped sanitary napkin wainscot. The elastic membrane is an elastic punched air-permeable membrane, that is, air-permeable holes in the elastic punched air-permeable membrane 22 are formed by punching with concave-convex roll sets, wherein cutter teeth of the concave-convex roll sets are conical concave-convex knife roll sets (that is, air-permeable holes in the elastic punched air-permeable membrane 22 are formed by extrusion with a conical head), and therefore, the air-permeable holes in the membrane surface of the elastic punched air-permeable membrane are conical holes 23.

Embodiment 13: refer to FIG. 7 and FIG. 1. A manufacturing method for an elastic air-permeable arc-shaped folded side-leakage-proof non-woven fabric is provided, wherein elastic macromolecular resin particles are cast into an elastic membrane via an elastic macromolecular resin cast membrane head, the elastic membrane is exported via elastic air-permeable cast membrane forming roll sets 2-1 and 2-2 to form an elastic air-permeable membrane 4 whose membrane surface is distributed with numerous air-permeable holes, the elastic punched air-permeable membrane 4 is longitudinally stretched in an S shape via multiple pairs of elastic air-permeable membrane stretching roll sets and then enters compound forming roll sets 7-1 and 7-2 together with unstretched non-woven fabric strips located on two sides of the elastic punched air-permeable membrane to be compounded by hot pressing and then exported, and then, the non-woven fabric strips located on two sides of the elastic punched air-permeable membrane 4 form an elastic arc-shaped wainscot, having a side-leakage-proof side wall, for sanitary napkins or panty-shape diapers with the rebound and reset of the elastic punched air-permeable membrane 4.

It needs to be understood that: a more detailed literal description is made for the design thought of the present invention in the above embodiments, but these literal descriptions are just simple literal descriptions to the design thought of the present invention, rather than limiting the design thought of the present invention. Any combination, addition or amendment which does not go beyond the design thought of the present invention should fall into the protection scope of the present invention.

The invention claimed is:

1. A manufacturing method for an elastic air-permeable arc-shaped folded composite nonwoven fabric, wherein elastic macromolecular resin particles are cast into an elastic membrane or an elastic air-permeable membrane via an elastic macromolecular resin cast membrane head, the elastic membrane is exported via elastic air-permeable cast membrane forming roll sets (2-1, 2-2) to form an elastic punched air-permeable membrane (4) whose membrane surface is distributed with numerous air-permeable holes, the elastic punched air-permeable membrane (4) or the elastic air-permeable membrane is longitudinally stretched in an S shape via multiple pairs of elastic air-permeable membrane stretching roll sets and then enters compound forming roll sets (7-1, 7-2) together with an unstretched underlayer non-woven fabric (8) and an unstretched face layer non-woven fabric (6) located on two sides of the elastic punched air-permeable membrane (4) to be compounded by hot pressing and then exported, and then, the face layer non-woven fabric (6) and the underlayer non-woven fabric (8) located on two sides of the elastic punched air-permeable membrane (4) form the elastic arc-shaped folded side-leakage-proof non-woven fabric with the rebound and reset of the elastic punched air-permeable membrane (4); or the elastic membrane is exported via elastic air-permeable cast membrane forming roll sets (2-1, 2-2) to form an elastic punched air-permeable membrane (4) whose membrane surface is distributed with numerous air-permeable holes, the elastic punched air-permeable membrane (4) or the elastic air-permeable membrane is longitudinally stretched in an S shape via multiple pairs of elastic air-permeable membrane stretching roll sets and then enters compound forming roll sets (7-1, 7-2) together with an unstretched underlayer non-woven fabric (8) and an unstretched face layer non-woven fabric (6) located on two sides of the elastic punched air-permeable membrane (4) to be compounded by hot pressing and then exported, and then, the face layer non-woven fabric (6) and the underlayer non-woven fabric (8) located on two sides of the elastic punched air-permeable membrane (4) form the elastic arc-shaped folded side-leakage-proof non-woven fabric with the rebound and reset of the elastic punched air-permeable membrane (4).

2. A manufacturing method for an elastic air-permeable arc-shaped folded composite nonwoven fabric, wherein elastic macromolecular resin particles are cast into an elastic membrane via an elastic macromolecular resin cast membrane head, the elastic membrane is exported via elastic air-permeable cast membrane forming roll sets (2-1, 2-2) to form an elastic punched air-permeable membrane (4) whose membrane surface is distributed with numerous air-permeable holes, the elastic punched air-permeable membrane (4) is longitudinally stretched in an S shape via multiple pairs of elastic air-permeable membrane stretching roll sets and then enters compound forming roll sets (7-1, 7-2) together with unstretched non-woven fabric strips located on two sides of the elastic punched air-permeable membrane (4) to be compounded by hot pressing and then exported, and then, the non-woven fabric strips located on two sides of the elastic punched air-permeable membrane (4) form an elastic arc-shaped wainscot, having a side-leakage-proof side wall, for sanitary napkins and the crotch of panty-shape diapers; or the elastic membrane is exported via elastic air-permeable cast membrane forming roll sets (2-1, 2-2) to form an elastic air-permeable membrane (4) whose membrane surface is distributed with numerous air-permeable holes, the elastic punched air-permeable membrane (4)is longitudinally stretched in an S shape via multiple pairs of elastic air-permeable membrane stretching roll sets and then enters compound forming roll sets (7-1, 7-2) together with unstretched non-woven fabric strips located on two sides of the elastic punched air-permeable membrane (4) to be compounded by hot pressing and then exported, and then, the non-woven fabric strips located on two sides of the elastic punched air-permeable membrane (4) form an elastic arc-shaped wainscot, having a side-leakage-proof side wall, for sanitary napkins and the crotch of panty-shape diapers.

3. A forming method for a folded side-leakage-proof arc-shaped elastic sanitary product wainscot, wherein the elastic membrane (2) or the elastic air-permeable membrane is prepared from elastic macromolecular resin particles under a molten state via a membrane forming process, or the elastic punched air-permeable membrane is formed from the elastic membrane by punching with a membrane punching roll set; and under a tensile state, after two sides of the elastic punched air-permeable membrane or the elastic air-permeable membrane are compounded with nonwoven fabrics (1) by hot pressing respectively, the elastic punched air-permeable membrane or the elastic air-permeable membrane rebounds and impels the nonwoven fabrics (1) at two sides to form a folded side-leakage-proof side wall with the rebound of the elastic punched air-permeable membrane or the elastic air-permeable membrane, wherein the elastic membrane (2) located between the nonwoven fabric strips is in the shape of a concave arc.

\* \* \* \* \*